United States Patent [19]
de Lacharriere et al.

[11] Patent Number: 5,730,998
[45] Date of Patent: Mar. 24, 1998

[54] USE OF A SUBSTANCE P ANTAGONIST FOR THE TREATMENT OF PRURITUS, OCULAR AND/OR PALPEBRAL PAIN AND OCULAR OR PALPEBRAL DYSAESTHESIA

[75] Inventors: Olivier de Lacharriere, Paris; Lionel Breton, Versailles, both of France

[73] Assignee: Société L'Oréal S.A., Paris, France

[21] Appl. No.: 574,853

[22] Filed: Dec. 19, 1995

[30] Foreign Application Priority Data

Dec. 19, 1994 [FR] France ................... 94 15255

[51] Int. Cl.$^6$ .................... A61F 13/02; A61F 2/02; A61K 9/48; A61K 9/20
[52] U.S. Cl. .................... 424/443; 424/423; 424/451; 424/464
[58] Field of Search .................... 424/443, 423, 424/451, 464

[56] References Cited

U.S. PATENT DOCUMENTS 5,565,462  10/1996  Eitan et al. .................... 514/262

FOREIGN PATENT DOCUMENTS

93/06099  4/1993  WIPO.

OTHER PUBLICATIONS

Database WPI, Section Ch, Week 9404, Derwent Publications Ltd., London, GB; Class B02, AN 94-031791 & JP-A-05,339,240, Dec. 21, 1993.

Proceedings of the National Academy of Sciences of USA, vol. 87, No. 12, Jun. 1, 1990, pp. 4833-4835, XP 000134336, Folkers et al, "Spantide II, An . . . ".

*Primary Examiner*—Carlos Azpuru
*Attorney, Agent, or Firm*—Burns, Doane, Swecker & Mathis, L.L.P.

[57] ABSTRACT

The invention relates to the use of a substance P antagonist in or for the preparation of a cosmetic or pharmaceutical composition, in particular for topical application, for treating pruritus, ocular or palpebral pain and ocular or palpebral dysaesthesia. The cosmetic composition may be used for making up sensitive eyes or removing make-up therefrom.

30 Claims, No Drawings

USE OF A SUBSTANCE P ANTAGONIST FOR THE TREATMENT OF PRURITUS, OCULAR AND/OR PALPEBRAL PAIN AND OCULAR OR PALPEBRAL DYSAESTHESIA

BACKGROUND OF THE INVENTION

1. Field of the Invention

The present invention relates to the use of a substance P antagonist for the preparation of a pharmaceutical composition for treating, in particular, topically, pruritus, ocular and/or palpebral dysaesthesia and ocular and/or palpebral pain, as well as to the use of a substance P antagonist in a cosmetic composition intended for the care or making-up of the eyes or eyelids.

Some patients suffer ocular and/or palpebral pain following operations or blows received on the eye. Moreover, some people very frequently experience sensations of itching or pruritus and dysaesethetic sensations on the eyes and eyelids without the exact cause of this being known.

Dysaesthetic sensations are understood to mean sensations of burning or inflammation, prickling, tingling, discomfort, tightness, and the like. These sensations may be associated with redness, nevertheless without this implying the presence of conjunctivitis.

These collective ophthalmic signs may, in addition, be associated with rosacea, independently of the existence of conjunctivitis.

Among the factors triggering ophthalmic or palpebral pruriginous or dysaesthetic attacks, rapid temperature changes, heat and, in particular, exposure to ultraviolet or infrared, relatively low humidity, exposure to buffeting winds or to drafts (blower fans, air conditioning), the application of surfactants, exposure to toxic or irritant vapours (solvents, etc.), irritant ophthalmological drops or topical preparations, irritant topical dermatological or cosmetic palpebral preparations (alpha-hydroxy acids, etc.) or the use of some cosmetics, even when the latter are not known to be especially irritant, may be mentioned.

2. Description of the Related Art

Hitherto, the mechanism of formation of these signs was very poorly understood, and ocular and/or palpebral dysaesthesia was treated with corticoids and also local antiseptics in the form of ophthalmic ointment or of drops.

Corticoids are relatively effective for calming the above symptoms, but unfortunately they display side-effects which are often very detrimental, such as atrophy. Furthermore, they sensitize to fungal or bacterial infections, and their speed of action is often slow (several minutes to a few hours). Moreover, their chronic use may lead to a drug dependency.

SUMMARY OF THE INVENTION AND DESCRIPTION OF PREFERRED EMBODIMENTS

Hence there remains the need for a treatment of ocular and palpebral pruritus, pain and dysaesthesia which does not have the above drawbacks.

The subject of the present invention is, in fact, the use of one or more substance P antagonists for treating these complaints.

Substance P is a polypeptide chemical component produced and released by a nerve ending. It belongs to the tachykinin family, tachykinins originating from the free sensory nerve endings of the epidermis and dermis. Substance P participates, in particular, in the transmission of pain and in central nervous system disorders such as anxiety and schizophrenia, in respiratory and inflammatory disorders, in gastrointestinal disorders, in rheumatic disorders and in certain skin disorders such as eczema, psoriasis, urticaria and contact dermatitis.

It is known to use substance P antagonists to treat the disorders mentioned above. To this end, reference may be made to the documents U.S. Pat. No. 4,472,305, U.S. Pat. No. 4,839,465, EP-A-101,929, EP-A-333,174, EP-A-336,230, EP-A-394,989, EP-A-443,132, EP-A-498,069, EP-A-515,681, EP-A-517,589, WO-A-92/22569, GB-A-2,216,529, EP-A-360,390, EP-A-429,366, EP-A-430,771, EP-A-499,313, EP-A-514,273, EP-A-514,274, EP-A-514,275, EP-A-514,276, EP-A-520,555, EP-A-528,495, EP-A-532,456, EP-A-545,478, EP-A-558,156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116, EP-A-522,808, WO-A-93/01165, WO-A-93/10073 and WO-A-94/08997.

However, nobody had envisaged hitherto using substance P antagonists for treating pruritus and/or ocular and/or palpebral pain and/or ocular or palpebral dysaesthesia.

Thus, the subject of the present invention is the use of at least one substance P antagonist for the preparation of a pharmaceutical or dermatological composition for treating pruritus and/or ocular and/or palpebral pain and/or ocular or palpebral dysaesthesia.

The application of compositions containing one or more substance P antagonists to the eyes or eyelids enables a marked decrease or even a complete disappearance of the ophthalmic pain, dysaesthetic sensations and pruritus to be obtained; a calming and soothing, preventive and curative effect on the eyes and eyelids is observed very quickly, and in any case much faster than with corticoids. In addition, no drug dependency is noted.

By means of these substance P antagonists, it is, in addition, possible to design cosmetic compositions for sensitive eyes, and especially eye make-up removal or cleansing lotions and make-up products for sensitive eyes, and in particular eyeshadows, mascaras, pencils or eyeliners for sensitive eyes.

Thus, the subject of the invention is also the use of at least one substance P antagonist in a cosmetic composition, containing a cosmetically acceptable medium, intended for sensitive eyes.

The composition of the invention contains a cosmetically, pharmaceutically or dermatologically acceptable medium, that is to say a medium compatible with the skin and the eyes. The composition containing the substance P antagonist is applied, in particular, topically. It may also be swallowed or injected.

For a substance to be recognized as a substance P antagonist, it must satisfy the following characteristic:

have a pharmacological activity antagonistic to substance P, that is to say induce a coherent pharmacological response in at least one of the following two tests:

the antagonist substance must decrease the extravasation of plasma through the vascular wall induced by capsaicin or by an antidromic nervous stimulation, or alternatively the antagonist substance must cause an inhibition of the smooth muscle contraction induced by the administration of substance P.

The substance P antagonist can, in addition, have a selective affinity for the tachykinin NK1 receptors.

The substance P antagonist of the invention may be functional or receptor-directed, that is to say may inhibit the synthesis and/or release of substance P, or prevent its binding and/or modulate its action.

The substance P antagonist of the invention can be, in particular, a peptide or a nitrogenous non-peptide derivative, and more specifically a compound containing a nitrogen, sulphur or oxygen heterocycle, or a compound comprising a nitrogen atom linked directly or indirectly to a benzene ring.

It is possible to use in the invention, for example, as a substance P antagonist peptide, sendide and spantide II.

Sendide Corresponds to the Formula

Tyr D-Phe Phe D-His Leu Met NH$_2$ in which:

Tyr represents tyrosine,
D-Phe represents D-phenylalanine,
Phe represents phenylalanine,
D-His represents D-histidine,
Leu represents leucine,
Met represents methionine.

Spantide II Corresponds to the Formula

D-NicLys Pro 3-Pal Pro D-Cl$_2$Phe Asn D-Trp Phe
D-Trp Leu Nle NH$_2$ in which:

D-NicLys represents D-lysine nicotinate,
Pro represents proline,
3-Pal represents 3-pyridylalanine,
D-Cl$_2$Phe represents D-dichlorophenylalanine,
Asn represents asparagine,
D-Trp represents D-tryptophan,
Phe represents phenylalanine,
Leu represents leucine,
Nle represents norleucine.

It is also possible to use in the invention, as a substance P antagonist peptide, the peptides described in the documents U.S. Pat. No. 4,472,305, U.S. Pat. No. 4,839,465, EP-A-101,929, EP-A-333,174, EP-A-336,230, EP-A-394,989, EP-A-443,132, EP-A-498,069, EP-A-515,681, EP-A-517,589, WO-A-92/22569 and GB-A-2,216,529.

The non-peptide substance P antagonists which can be used in the invention are, in particular, heterocyclic compounds, in particular heterocyclic nitrogen, sulphur or oxygen compounds, or compounds comprising a nitrogen atom linked directly or indirectly to one or more benzene rings.

As a heterocyclic compound, those containing a nitrogen heterocycle and which are described in the following documents may be used in the invention:

EP-A-360,390, EP-A-429,366, EP-A-430,771, EP-A-499,313, EP-A-514,273, EP-A-514,274, EP-A-514,275, EP-A-514,276, EP-A-520,555, EP-A-528,495, EP-A-532,456, EP-A-545,478, EP-A-558,156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116 and WO-A-94/08997. In particular, the compound comprising at least one nitrogen heterocycle is a 2-tricyclyl-2-aminoethane derivative, a spirolactam derivative, a quinuclidine derivative, an azacyclic derivative, an aminopyrrolidine derivative, a piperidine derivative, an aminoazaheterocycle or an isoindole derivative.

As other heterocyclic compounds, there may be mentioned heterocyclic oxygen or sulphur compounds such as furan derivatives, benzofuran derivatives, thiophene derivatives and benzothiophene derivatives, optionally containing nitrogenous substituents, such as the heterocyclic compounds described in the documents U.S. Pat. No. 4,931,459, U.S. Pat. No. 4,910,317 and EP-A-299,457, and more especially alkoxy- and/or aryloxytetrazolylbenzofurancarboxamides or alkoxy- and/or aryloxytetrazolylbenzothiophenecarboxamides.

As compounds containing a nitrogen atom linked directly or indirectly to a benzene ring, those described in the following documents may be mentioned: EP-A-522,808, WO-A-93/01165 and WO-A-93/10073. Ethylenediamine derivatives such as N,N'-bis[bis(3,5dimethylbenzyl)] ethylenediamine or N,N'-bis[bis(3,5dimethoxybenzyl)] ethylenediamine may be mentioned in particular; these compounds are described as synthesis intermediates in the document WO-A-93/11338 filed in the name of the Applicant.

The substance P antagonists may be synthesized or extracted from natural products (plant or animal).

In the compositions according to the invention, the substance P antagonist is preferably used in an amount ranging from 0.000001 to 5% by weight relative to the total weight of the composition, and especially in an amount ranging from 0.0001 to 0.1% by weight relative to the total weight of the composition.

The compositions of the invention may be presented in all pharmaceutical dosage forms normally used for topical application; the composition may take the form, in particular, of aqueous, aqueous-alcoholic or oily solutions or of dispersions of the lotion or serum type, of emulsions of liquid or semi-liquid consistency of the milk type, obtained by dispersing a fatty phase in an aqueous phase (O/W) or vice versa (W/O), or of suspensions or emulsions of soft, semi-solid or solid consistency of the cream or gel type, of microemulsions, of microcapsules, of microparticles, of vesicular dispersions of the ionic and/or nonionic type or of compacted or poured powders. These compositions are prepared according to the standard methods.

For topical application for therapeutic purposes, the compositions take the form, in particular, of an eye lotion, ointment or eye wash solution. For cosmetic application, the compositions can consist, in particular, of creams for the care or protection of sensitive eyes, of cleansing or make-up removal milks or lotions for sensitive eyes, or of make-up products for eyes which are, in particular, sensitive, such as pencils, mascaras, eyeliners and eye shadows.

The injectable compositions may take the form of an aqueous or oily lotion or the form of a serum.

The compositions used orally may take the form of capsules, including hard gelatin capsules, of syrups or of tablets.

The amounts of the different constituents of the compositions according to the invention are those traditionally used in the fields in question.

When the composition of the invention is an emulsion, the proportion of the fatty phase can range from 5% to 80% by weight, and preferably from 5% to 50% by weight, relative to the total weight of the composition. The oils, emulsifiers and coemulsifiers used in the composition in emulsion form are chosen from those traditionally used in the cosmetics and dermatological fields. The emulsifier and the coemulsifier are present in the composition in a proportion ranging from 0.3 to 30% by weight, and preferably from 0.5 to 20% by weight, relative to the total weight of the composition. The emulsion can, in addition, contain lipid vesicles.

When the composition is an oily gel or solution, the amount of oil can range up to more than 90% by weight of the total weight of the composition.

In a known manner, the composition of the invention can also contain adjuvants which are customary in the fields in question, such as hydrophilic or lipophilic gelling agents, hydrophilic or lipophilic active agents, preservatives, antioxidants, solvents, perfumes, fillers, sunscreen agents, odour adsorbers, pigments and colouring matter. The amounts of these different adjuvants are those traditionally used in the fields in question, and are, for example, from 0.01% to 10% of the total weight of the composition. These adjuvants, depending on their nature, may be introduced into the fatty phase, into the aqueous phase and/or into lipid spherules.

As oils which can be used in the invention, mineral oils (liquid paraffin), vegetable oils (liquid fraction of shea butter, sunflower oil), animal oils (perhydrosqualene), synthetic oils (Purcellin oil), silicone oils (cyclomethicone) and fluorinated oils (perfluoro polyethers) may be mentioned. Fatty alcohols, fatty acids (stearic acid) or alternatively waxes (paraffin, carnauba, beeswax) may also be used.

As emulsifiers which can be used in the invention, glyceryl stearate, polysorbate 60 and the PEG-6/PEG-32/glycol stearate mixture sold under the name Tefose® 63 by the company Gattefosse may be mentioned as examples.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids such as aluminium stearates, hydrophobic silica, polyethylenes and ethylcellulose may be mentioned.

As hydrophilic active agents, proteins or protein hydrolysates, amino acids, polyols, urea, allantoin, sugars and sugar derivatives, vitamins and plant extracts in particular of Aloe vera, may be used.

As lipophilic active agents, tocopherol (vitamin E) and its derivatives, retinol (vitamin A) and its derivatives, essential fatty acids, ceramides and essential oils may be used.

It is also possible to combine the substance P antagonists with active agents, in particular cicatrizing (for example vitamin $B_{12}$), antiseptic (for example boric acid), anti-allergic (for example sodium cromoglycate), antiviral (for example acyclovir), anaesthetic (for example lidocaine hydrochloride and derivatives) and non-steroidal anti-inflammatory (for example indomethacin) agents.

The examples which follow illustrate the invention. In these examples, the proportions shown are percentages by weight.

Example 1

Eye Lotion

Sendide 0.5%
Excipient: qs 100%
   Sodium chloride
   Sodium borate
   Polysorbate 80
   Boric acid
   Water Example 2

Ointment

N,N'-Bis[bis(3,5-dimethoxybenzyl)]ethylenediamine 1%
Excipient: qs 100%
   Benzalkonium chloride
   Sodium edetate
   D-Mannitol
   Carbomer
   Sodium hydroxide
   Water Example 3

Solution

Spantide II 2%
Excipient:
   Boric acid 5%
   Sodium chloride 0.3%
   Phenyl mercury borate 0.5%
   Water qs 100%

Example 4

Ointment

This example differs from Example 2 by the use as substance P antagonist of 3-benzyloxy-5-methoxy- N-(1H-tetrazol-5-yl)benzothiophene-2-carboxamide, manufactured according to Example 1 of the document EP-A-299,457.

We claim:

1. A method for treating pruritus and/or ocular and/or palpebral pain and/or ocular or palpebral dysaesthesia, comprising administering a pharmaceutical composition containing a therapeutically effective amount of at last one substance P antagonist contained in a pharmaceutically acceptable medium.

2. A method for treating sensitive eyes comprising administering a cosmetic composition comprising an effective amount of at least one substance P antagonist contained in a cosmetically acceptable medium.

3. The method according to claim 1, wherein the substance P antagonist is selected from the group consisting of peptides, compounds comprising at least one heterocycle and nitrogen compounds comprising one or more benzene rings.

4. The method according to claim 2, wherein the substance P antagonist is selected from the group consisting of peptides, compounds comprising at least one heterocycle and nitrogen compounds comprising one or more benzene rings.

5. The method according to claim 1, wherein said peptide is sendide or spantide II.

6. The method according to claim 2, wherein said peptide is sendide or spantide II.

7. The method according to claim 1, wherein said substance P antagonist comprising at least one heterocycle is a heterocyclic nitrogen compound selected from the group consisting of 2-tricyclyl-2-aminoethane derivatives, spirolactam derivatives, quinuclidine derivatives, azacyclic derivatives, aminopyrrolidine derivatives, piperidine derivatives, aminoazaheterocycles and isoindole derivatives.

8. The method according to claim 2, wherein said substance P compound comprising at least one heterocycle is a heterocyclic nitrogen compound selected from the group consisting of 2-tricyclyl-2-aminoethane derivatives, spirolactam derivatives, quinuclidine derivatives, azacyclic derivatives, aminopyrrolidine derivatives, piperidine derivatives, aminoazaheterocycles and isoindole derivatives.

9. The method according to claim 3, wherein said compound comprising at least one heterocycle is a heterocyclic oxygen or sulphur compound selected from the group consisting of furan derivatives, benzofuran derivatives, thiophene derivatives and benzothiophene derivatives.

10. The method according to claim 4, wherein said compound comprising at least one heterocycle is a heterocyclic oxygen or sulphur compound selected from the group consisting of furan derivatives, benzofuran derivatives, thiophene derivatives and benzothiophene derivatives.

11. The method of claim 9, wherein said benzothiophene derivative is a tetrazolylbenzofurancarboxamide or tetrazolylbenzothiophenecarboxamide.

12. The method of claim 10, wherein said benzothiophene derivative is a tetrazolylbenzofurancarboxamide or tetrazolylbenzothiophenecarboxamide.

13. The method according to claim 1, wherein the substance P antagonist is an ethylenediamine derivative containing at least one benzene ring.

14. The method according to claim 2, wherein the substance P antagonist is an ethylenediamine derivative containing at least one benzene ring.

15. The method according to claim 1, wherein the substance P antagonist contained in the administered composition is comprised in an amount ranging from 0.000001 to 5% by weight relative to the total weight of the composition.

16. The method according to claim 2, wherein the substance P antagonist contained in the administered composition is comprised in an amount ranging from 0.000001 to 5% by weight relative to the total weight of the composition.

17. The method according to claim 1, wherein the substance P antagonist contained in the administered composition is comprised in an amount ranging from 0.0001 to 0.1% by weight relative to the total weight of the composition.

18. The method according to claim 2, wherein the substance P antagonist contained in the administered composition is comprised in an amount ranging from 0.0001 to 0.1% by weight relative to the total weight of the composition.

19. The method according to claim 1, wherein the administered composition contains, in addition, at least one active agent selected from the group consisting of proteins, protein hydrolysates, amino acids, polyols, urea, sugars, sugar derivatives, vitamins, starches, plant extracts, ceramides and essential oils.

20. The method according to claim 2, wherein the administered composition contains, in addition, at least one active agent selected from the group consisting of proteins, protein hydrolysates, amino acids, polyols, urea, sugars, sugar derivatives, vitamins, starches, plant extracts, ceramides and essential oils.

21. The method according to claim 1, wherein the administered composition contains, in addition, at least one agent selected from the group consisting of cicatrizing, antiseptic, anti-allergic, anaesthetic, antiviral and non-steroidal anti-inflammatory agents.

22. The method according to claim 2, wherein the administered composition contains, in addition, at least one agent selected from the group consisting of cicatrizing, antiseptic, anti-allergic, anaesthetic, antiviral and non-steroidal anti-inflammatory agents.

23. The method according to claim 1, wherein the composition is administered orally, topically, or by injection.

24. The method according to claim 2, wherein the composition is administered orally, topically, or by injection.

25. The method according to claim 11, wherein the administered composition is selected from the group consisting of aqueous, oily, aqueous-alcoholic solutions, water-in-oil emulsions, oil-in-water emulsions, microemulsions, aqueous gels, anhydrous gels, serums, dispersions of vesicles, dispersions of microcapsules, dispersions of microparticles, and compacted powders and poured powders.

26. The method according to claim 2, wherein the administered composition is selected from the group consisting of aqueous, oily, aqueous-alcoholic solutions, water-in-oil emulsions, oil-in-water emulsions, microemulsions, aqueous gels, anhydrous gels, serums, dispersions of vesicles, dispersions of microcapsules, dispersions of microparticles, and compacted powders and poured powders.

27. The method according to claim 1, wherein the administered composition is an eye make-up or eye make-up remover.

28. The method according to claim 2, wherein the administered composition is an eye make-up or eye make-up remover.

29. The method according to claim 1, wherein the composition contains, in addition, at least one adjuvant selected from the group consisting of emulsifiers, preservatives, antioxidants and solvents.

30. The method according to claim 2, wherein the composition contains, in addition, at least one adjuvant selected from the group consisting of emulsifiers, preservatives, antioxidants and solvents.

* * * * *